(12) United States Patent
Korhonen et al.

(10) Patent No.: US 9,269,000 B2
(45) Date of Patent: Feb. 23, 2016

(54) METHOD AND APPARATUS FOR PROVIDING ADAPTIVE DISPLAY AND FILTERING OF SENSORS AND SENSOR DATA

(71) Applicant: Nokia Corporation, Espoo (FI)

(72) Inventors: Ilkka Korhonen, Espoo (FI); Jari Olavi Nousiainen, Espoo (FI); Tero Markuu Makela, Espoo (FI)

(73) Assignee: NOKIA TECHNOLOGIES OY, Espoo (FI)

( * ) Notice: Subject to any disclaimer, the term of this patent is extended or adjusted under 35 U.S.C. 154(b) by 631 days.

(21) Appl. No.: 13/663,285

(22) Filed: Oct. 29, 2012

(65) Prior Publication Data

US 2013/0060480 A1    Mar. 7, 2013

Related U.S. Application Data

(63) Continuation-in-part of application No. 13/194,207, filed on Jul. 29, 2011, now abandoned.

(51) Int. Cl.

| | |
|---|---|
| *G01R 15/00* | (2006.01) |
| *G01R 29/00* | (2006.01) |
| *G06F 17/40* | (2006.01) |
| *G06F 19/00* | (2011.01) |
| *G06K 9/00* | (2006.01) |
| *H03H 21/00* | (2006.01) |
| *A61B 5/00* | (2006.01) |
| *A61B 5/04* | (2006.01) |
| *A61B 5/11* | (2006.01) |
| *G06K 9/62* | (2006.01) |
| *G06K 9/68* | (2006.01) |

(52) U.S. Cl.
CPC ........ *G06K 9/00536* (2013.01); *A61B 5/04017* (2013.01); *A61B 5/1118* (2013.01); *A61B 5/721* (2013.01); *A61B 5/725* (2013.01); *G06K 9/6293* (2013.01); *G06K 9/685* (2013.01); *H03H 21/0012* (2013.01); *A61B 5/0006* (2013.01); *A61B 5/0022* (2013.01); *A61B 5/0024* (2013.01); *A61B 2560/0209* (2013.01); *A61B 2562/0219* (2013.01); *G01R 15/00* (2013.01); *G01R 29/00* (2013.01); *G06F 17/40* (2013.01); *G06F 19/00* (2013.01)

(58) Field of Classification Search
None
See application file for complete search history.

(56) References Cited

U.S. PATENT DOCUMENTS

| | | | | |
|---|---|---|---|---|
| 2,883,255 | A * | 4/1959 | Anderson | 346/34 |
| 5,247,245 | A * | 9/1993 | Nelson | 324/133 |
| 2013/0030711 | A1 * | 1/2013 | Korhonen | 702/19 |

* cited by examiner

*Primary Examiner* — Edward Cosimano
(74) *Attorney, Agent, or Firm* — Ditthavong & Steiner, P.C.

(57) ABSTRACT

An approach is provided for adaptive display and filtering of sensors and sensor data. A sensor manager determines one or more signals associated with one or more sensors. The sensor manager then processes and/or facilitates a processing of the one or more signals for comparison against one or more predetermined signals. The sensor manager determines one or more parameters for one or more filters based, at least in part, on the comparison, wherein the one or more filters operate, at least in part, on the one or more sensors, one or more other signals determined form the one or more sensors, or a combination thereof.

26 Claims, 11 Drawing Sheets

METHOD AND APPARATUS FOR PROVIDING ADAPTIVE DISPLAY AND FILTERING OF SENSORS AND SENSOR DATA

PRIORITY CLAIM AND CROSS-REFERENCE TO RELATED APPLICATIONS

This application is a continuation-in-part of abandoned U.S. application Ser. No. 13/194,207 entitled "Method and Apparatus for Providing Adaptive Filtering of Sensors and Sensor Data" filed Jul. 29, 2012, the entireties of which are incorporated herein.

BACKGROUND

Service providers (e.g., wireless, cellular, etc.) and device manufacturers are continually challenged to deliver value and convenience to consumers by, for example, providing compelling network services. One area of development has been the integration of sensors and filters for determining contextual information for use in network services to enable such services to be, for instance, adaptive systems. For example, adaptive systems use knowledge about a user's current situation to tailor system services, functions, content, etc. in a situationally-appropriate manner based on data collected from one or more sensors. These sensors may include health and wellness sensors such as electrocardiograph (ECG) sensors, photoplethysmograph (PPG) sensors, galvanic skin response (GSR) sensors, and the like. As use of such sensors become more common, service providers and device manufacturers face significant challenges to enabling the sensors to operate continuously for prolonged periods, particularly when the sensors operate on limited battery power.

SOME EXAMPLE EMBODIMENTS

Therefore, there is a need for an approach for providing adaptive display and filtering of sensors and sensor data while maximizing, for instance, energy efficiency and data quality.

According to one embodiment, a method comprises determining one or more signals associated with one or more sensors, the one or more sensors associated with determining at least one operational state of one or more sensors. The method also comprises processing and/or facilitating a processing of the one or more signals for comparison against one or more predetermined signals. The method further comprises determining one or more parameters for one or more filters based, at least in part, on the comparison, wherein the one or more filters operate, at least in part, on the one or more sensors, one or more other signals determined form the one or more other sensors, or a combination thereof.

According to another embodiment, an apparatus comprising at least one processor, and at least one memory including computer program code, the at least one memory and the computer program code configured to, with the at least one processor, cause, at least in part, the apparatus to determine one or more signals associated with one or more sensors, the one or more sensors associated with determining at least one operational state of one or more sensors. The apparatus is also caused to process and/or facilitate processing of the one or more signals for comparison against one or more predetermined signal. The apparatus is further caused to determine one or more parameters for one or more filters based, at least in part, on the comparison, wherein the one or more filters operate, at least in part, on the one or more sensors, one or more other signals determined form the one or more other sensors, or a combination thereof.

According to another embodiment, a computer-readable storage medium carrying one or more sequences of one or more instructions which, when executed by one or more processors, cause, at least in part, an apparatus to determine one or more signals associated with one or more sensors, the one or more sensors associated with determining at least one operational state of one or more sensors. The apparatus is also caused to process and/or facilitate processing of the one or more signals for comparison against one or more predetermined signal. The apparatus is further caused to determine one or more parameters for one or more filters based, at least in part, on the comparison, wherein the one or more filters operate, at least in part, on the one or more sensors, one or more other signals determined form the one or more other sensors, or a combination thereof.

According to another embodiment, an apparatus comprises means for determining one or more signals associated with one or more sensors, the one or more sensors associated with determining at least one operational state of one or more sensors. The apparatus also comprises means for processing and/or facilitating a processing of the one or more signals for comparison against one or more predetermined signals. The apparatus further comprises means for determining one or more parameters for one or more filters based, at least in part, on the comparison, wherein the one or more filters operate, at least in part, on the one or more sensors, one or more other signals determined form the one or more other sensors, or a combination thereof.

In addition, for various example embodiments of the invention, the following is applicable: a method comprising facilitating a processing of and/or processing (1) data and/or (2) information and/or (3) at least one signal, the (1) data and/or (2) information and/or (3) at least one signal based, at least in part, on (including derived at least in part from) any one or any combination of methods (or processes) disclosed in this application as relevant to any embodiment of the invention.

For various example embodiments of the invention, the following is also applicable: a method comprising facilitating access to at least one interface configured to allow access to at least one service, the at least one service configured to perform any one or any combination of network or service provider methods (or processes) disclosed in this application.

For various example embodiments of the invention, the following is also applicable: a method comprising facilitating creating and/or facilitating modifying (1) at least one device user interface (UI) element and/or (2) at least one device user interface functionality, the (1) at least one device user interface element and/or (2) at least one device user interface functionality based, at least in part, on data and/or information resulting from one or any combination of methods or processes disclosed in this application as relevant to any embodiment of the invention, and/or at least one signal resulting from one or any combination of methods (or processes) disclosed in this application as relevant to any embodiment of the invention.

For various example embodiments of the invention, the following is also applicable: a method comprising creating and/or modifying (1) at least one device user interface element and/or (2) at least one device user interface functionality, the (1) at least one device user interface element and/or (2) at least one device user interface functionality based at least in part on data and/or information resulting from one or any combination of methods (or processes) disclosed in this application as relevant to any embodiment of the invention, and/or at least one signal resulting from one or any combination of methods (or processes) disclosed in this application as relevant to any embodiment of the invention.

In various example embodiments, the methods (or processes) can be accomplished on the service provider side or on the mobile device side or in any shared way between service provider and mobile device with actions being performed on both sides.

For various example embodiments, the following is applicable: An apparatus comprising means for performing the methods disclosed herein.

Still other aspects, features, and advantages of the invention are readily apparent from the following detailed description, simply by illustrating a number of particular embodiments and implementations, including the best mode contemplated for carrying out the invention. The invention is also capable of other and different embodiments, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

The embodiments of the invention are illustrated by way of example, and not by way of limitation, in the figures of the accompanying drawings.

DESCRIPTION OF SOME EMBODIMENTS

Examples of a method, apparatus, and computer program for providing adaptive display and filtering of sensors and sensor data are disclosed. In the following description, for the purposes of explanation, numerous specific details are set forth in order to provide a thorough understanding of the embodiments of the invention. It is apparent, however, to one skilled in the art that the embodiments of the invention may be practiced without these specific details or with an equivalent arrangement. In other instances, well-known structures and devices are shown in block diagram form in order to avoid unnecessarily obscuring the embodiments of the invention.

Although various embodiments are discussed with respect to health and wellness sensors, it is contemplated that embodiments of the approach described herein are applicable to any type of sensor including environmental sensors, sensors for physical properties, material sensors, location sensors, etc.

Figure 1:
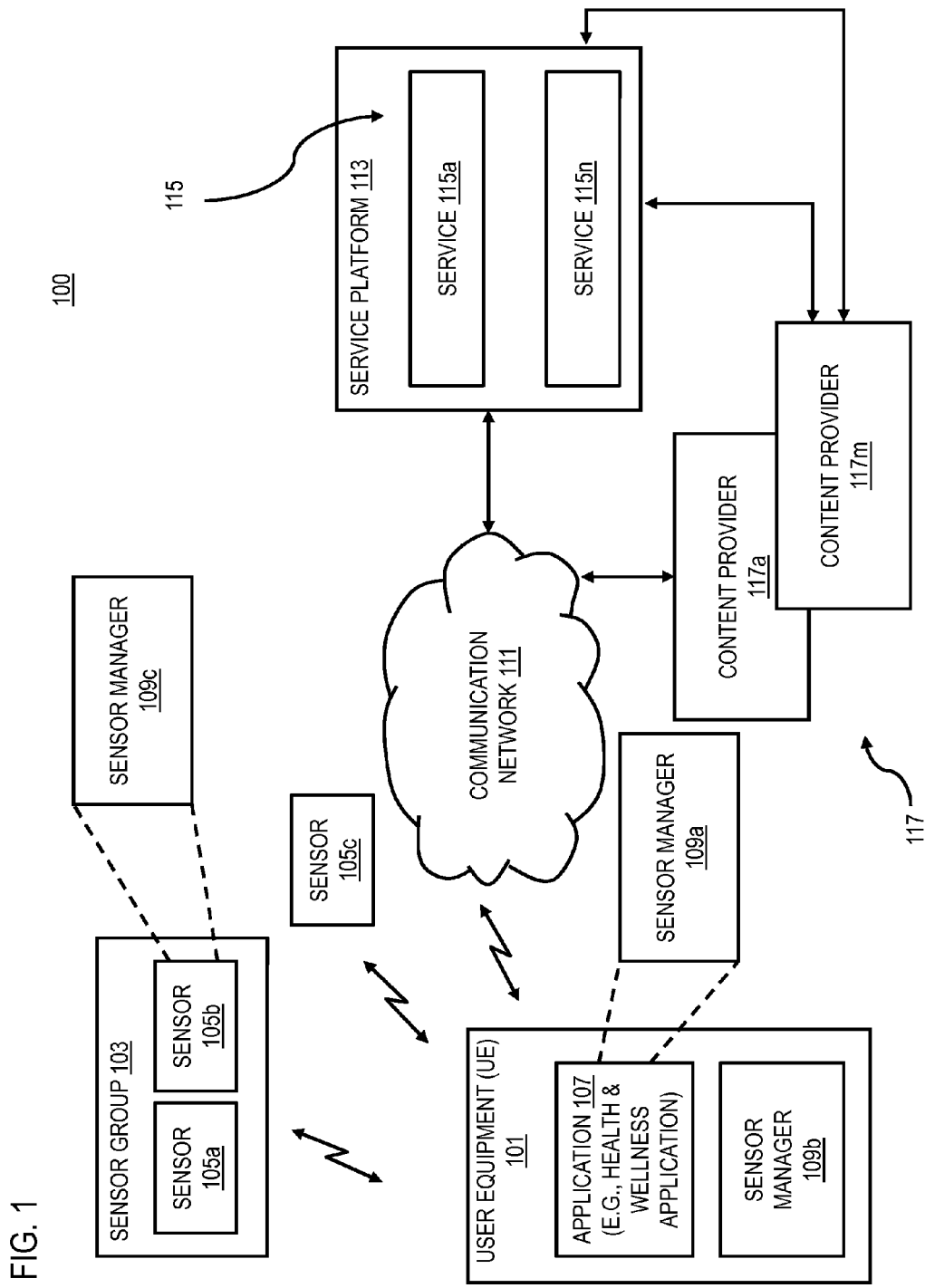
FIG. 1 is a diagram of a system capable of providing adaptive display and filtering of sensors and sensor data, according to one embodiment.

FIG. 1 is a diagram of a system capable of providing adaptive display and filtering of sensor and sensor data, according to one embodiment. As discussed above, the adaptation of a system or service is often based on sensor data. For example, possible sensors that may be associated with devices (e.g., mobile devices such as cell phones, smartphones, etc.) include location sensors (e.g., Global Positioning System (GPS) sensors, light sensors, proximity sensors, accelerometers, gyroscopes, etc.).

Within the context of systems for supporting health and wellness services and/or applications, possible sensors include electrocardiograph (ECG) sensors, photoplethysmograph (PPG) sensors, galvanic skin response (GSR) sensors, electroencephalograph (EEG) sensors, electromyography (EMG) sensors, and the like. In one embodiment, the health and wellness sensors support body sensor network (BSN) technologies that offer opportunities for monitoring physiological signals with wearable sensors in a mobile environment. For example, ECG-based wearable sensors enable continuous (e.g., 24-hours, every day, etc.) or substantially continuous monitoring for emotion monitoring and/or monitoring for cardiovascular disease.

In one embodiment, such monitoring is used to support pervasive healthcare which has drawn the attention in research communities such as ubiquitous computing, bio-engineering, and medical informatics because of the potential for the monitoring to provide longitudinal and quantitative personal data collection. The reliability and continuous nature of such monitoring is one key element in a program to maintain user wellness. As noted, a main component to support pervasive healthcare is a BSN system. In one embodiment, a BSN system includes use of wireless sensor nodes with smaller size, longer battery life, and powerful computing capabilities.

However, the operating lifetime of the physiological sensor is a key challenge in continuous monitoring design. More specifically, sensors may potentially require a significant amount of battery power (relative to the capacity of a battery on a small device) to operate continuously. Accordingly, extending and optimizing battery life (e.g., reducing energy consumption) is a significant challenge for service providers and device manufacturers. In other words, in order to offer the continuous monitoring and real-time or substantially real-time collection and analysis of sensor data, the BSN and its sensors need sufficient efficiency with respect to energy consumption to sense, transmit, display, and/or process the sensor data stream. For example, a wearable ECG sensor (or other wearable sensors such as a PPG sensor) cannot function effectively if battery life is limited to only a few hours. In particular, limited battery life and/or inefficient use of available energy reserves (e.g., battery life) can be further exacerbated with high data rate physiological sensors or high use of wireless transceivers to transmit the data from the sensors. In other cases, reducing energy consumption by the sensors also enables design of smaller, lighter, and more wearable sensor designs. In one embodiment, to reduce battery usage, sensor sampling may be made selective based on the likelihood of the sensor context to yield good data. Sensors may be set to sample only when context circumstances of the sensor are favourable to useful data collection. To further save energy or in the alternative, energy consumption may be reduced in the filtering process. Even where energy is saved by controlling sensors to collect data selectively, there is still the issue of energy consumption in the noise cancellation process for collected physiological samples. Cancellation of movement artifacts from the physiological signal is usually based on adaptive filtering, where movement signal is the reference signal $s(n)+N_0(n)$ and the movement artifact corrupted physiological signal is the primary signal $x(n)$. Typically, the adaptation of the noise cancellation filter $w(n)$ to optimally remove the noise (movement artifact) from $x(n)$ requires some time for adaptation, and therefore the sampling period cannot be very short when the movement artifact is present. Sampling to find the adaptation of the noise cancellation filter consumes energy. Minimizing the sampling time needed to adapt to the collected signal would reduce the overall energy consumption of the wearable sensors. Additionally, displaying of appropriate sensor data; for example, analysis, results, statistics, and the like, can add to energy consumption and processing requirements.

To address these problems, a system 100 of FIG. 1 presents an intelligent model-based adaptation algorithm. More specifically, a system 100 of FIG. 1 introduces the capability of using signals conveying context information (e.g., sensor data) detected or otherwise collected at one or more sensors to determine an operational state of one or more other sensors (e.g., health and wellness sensors) in order to determine one or more parameters for the adaptation of one or more filters. The signals include, at least in part, movement signals (e.g., due to user movement, device movement, etc.), physiological signals, models of movement signals (e.g., walking, jogging, etc.), models of physiological signals, or a combination thereof. As used herein, an operational state refers to an operating condition (e.g., enabled or disabled), one or more operating parameters (e.g., sampling rate, sampling start or end, sampling parameters, etc.). Further, the signals may be processed for determining one or more UI states for presenting one or more sensor data at one or more devices.

In one embodiment, the operational state is determined to identify one or more parameters by which one or more filters associated with the operational state may be applied to one or more other sensors. As used herein, an operational state refers to an operating condition (e.g., enabled or disabled), one or more operating parameters (e.g., sampling rate, sampling start or end, sampling parameters, etc.). In one embodiment, the operational state is determined to reduce resource consumption (e.g., energy consumption, bandwidth consumption, processing consumption, etc.) by the one or more other sensors. In this scenario, the parameters include initiation data, one or more coefficients determined from the initiation data, or a combination thereof. In one embodiment, the one or more filters include one or more adaptive filters. In this way, resources can be conserved to prolong the operational life or time of the sensors before one or more of the resources has to be replenished (e.g., recharging or replacing a sensor's battery) since adaptive filtering specific to the operational state is applied as soon as the operational state is identified, thus replacing a longer sampling period which would require more power consumption.

In one embodiment, in the context of health and wellness sensors (e.g., a wearable ECG sensor or PPG sensor), the system 100 can determine context information at another sensor or sensors (e.g., an accelerometer, gyroscope, compass, etc.) to determine when to enable or disable one or more of the associated filters and/or their functions to conserve resources and filter the sensor in accordance with the context.

For example, many sensors measure physiological characteristics of a user. Historically, these measurements consume a lot of energy because of the lag between sensing a signal and being able to apply a suitable noise cancellation algorithm to filter the signal. Accordingly, in one embodiment, the system 100 uses an individual's physical activity (e.g., resting, exercising, asleep, etc.) level to reduce energy consumption by identifying the physical activity of an individual and/or one or more parameters/limits associated with the user (e.g., default, predefined, etc.) and subsequently engaging a filter or filter algorithm associated with that type of physical activity. Previous art lacks the step of activating filter adaptation in response to a pre-set, corresponding model (such as physical activity), so energy is consumed in a relatively long period of sampling before adaptive filtering may be applied. The present system shortens the sampling period by identifying a means of adaptation without extended sampling, thus saving energy. In various embodiments, user information may be utilized to further define various parameters of a filter or a filter algorithm. For example, a baseline value range (e.g., min-max) for heart-rate measurements may be established by utilizing information about the user's age, gender, height, weight, physical condition, and the like. Further, various measurements of physiological signals; for example, heart-rate measurements over a certain period of time during various activities, may be utilized to augment and/or establish one or more baseline value ranges.

For example, assuming the user is wearing a first sensor or group of sensors that captures acceleration and a second sensor or group of sensors that captures physiological data such as heart rate signals, the system 100 determines the user's movement state using the accelerometer data. In one embodiment, the movement state is categorized into classes such as "walking" or "running" In addition or alternatively, the movement state can be described using a numerical metric or other ordinal scale. In either case, the system 100 recognizes the movement and triggers one or more relevant parameters to engage one or more filters associated with filtering signals corresponding to that particular movement state. Using the context information collected at the first sensor or group of sensors (e.g., the accelerometer data) to tailor filtering of data and/or processing at the second sensor or group of sensors enables the system 100 to save resources (e.g., battery life of the sensor) by minimizing the sampling period before filtering is adjusted to the context.

In one embodiment, one or more sensors may display and/or cause one or more devices to display information associated with the captured data. For example, a sensor may include a display wherein the information may be displayed for viewing and/or for possible user interaction. In one embodiment, a sensor may cause another sensor and/or a device to display the information. For example, a sensor may transmit captured data for display at a user device (e.g., a mobile device.) In various embodiments, displaying of the information and/or the data may be triggered and/or controlled based, at least in part, on the measuring device, display timer, values associated with the data, analysis of the information and/or data, user preferences, device status (e.g., battery status), data sampling rate, and the like.

As shown in FIG. 1, the system 100 includes a user equipment (UE) 101 with connectivity to at least one sensor group 103 including sensors 105a (e.g., a first sensor) and 105b (e.g., a second sensor). In one embodiment, the sensor group 103 constitutes a wearable sensor in which multiple sensors (e.g., sensors 105a and 105b) are included to provide additional functionality. For example, as described above, the sensor group 103 may include a combination of an accelerometer (e.g., sensor 105a) and a physiological sensor (e.g., sensor 105b) such as an ECG sensor or PPG sensor. As shown, the UE 101 also has connectivity to a standalone sensor 105c that can operate independently or in coordination with the sensor group 103 or other sensor groups or sensors. In one embodiment, the sensor group 103 and/or the sensors 105a-105c (also collectively referred to as sensors 105) may comprise a BSN. By way of example, connectivity between the UE 101 and the sensor group 103 and the sensors 105a-105c can be facilitated by short range wireless communications (e.g., BLUETOOTH wireless technology standard, WI-FI local area wireless networking technology, ANT/ANT+ powered nodes/interoperable wireless transfer capability, ZIGBEE wireless network standard, etc.). In various embodiments, any or all of the sensors may include one or more display devices for displaying one or more data and/or information items, which may be measured and/or determined by any of the sensors.

In addition, the UE 101 can execute an application 107 that is a software client for storing, processing, and/or forwarding the sensor data to other components of the system 100. In one embodiment, the application 107 may include a sensor manager 109a for performing functions related to providing adaptive display and filtering of the sensor group 103 and/or the sensors 105a-105c as discussed with respect to the various embodiments of the approach described herein. In addition or alternatively, it is contemplated that the UE 101 may include a standalone sensor manager 109b that operates independently of the application 107, and that the sensors themselves may include a sensor manager 109c (e.g., as shown with respect to sensor 105b).

As shown in FIG. 1, the UE 101 has connectivity via a communication network 111 to a service platform 113 which includes one or more services 115a-115n (e.g., health and wellness service or any other service that can use adaptive display and filtering of sensor information), the one or more content providers 117a-117m (e.g., online content retailers, public databases, etc.). In one embodiment, the sensors 105a-105c, the sensor managers 109a-109c (also collectively referred to as sensor managers 109), and or the application 107 can transmit sensor data to the service platform 113, the services 115a-115n, and/or the content providers 117a-117m for storage, processing, and/or further transmission.

In one sample use case, a user wears the sensor group 103 and/or the sensors 105a-105c for continuous monitoring and collection of sensor data (e.g., for continuous ECG monitoring). For such ECG monitoring, in an ideal case, the user wearing a sensor is stationary when a measurement is taken to reduce potential movement artifacts in the data. For example, the sensor group 103 transmits accelerometer and ECG information to the UE 101 at periodic intervals. The UE 101 (e.g., via the application 107 and/or the sensor manager 109b) stores the data temporarily, performs any needed processing and aggregation, and sends the data to one or more of the services at periodic intervals. In one embodiment, the data sent includes, at least in part, timestamps, sensor data (e.g., physiological data), and/or context information (e.g., activity level determined from the accelerometer data).

By way of example, the operational states of the sensors 105 may include setting and/or modifying related operational parameters including sampling rate, parameters to sample, transmission protocol, activity timing, etc. In certain embodiments, the sensor manager 109 can process and/or facilitate a processing of the context information and the resource consumption information to determine a schedule for performing at least one of the one or more functions on one or more filters.

When a sampling period starts, the context information (e.g., accelerometer data) indicates movement of the sensor group 103 and/or the sensors 105. Then, the sensor manager 109 will, for instance: (1) compare the data from sensors 105 against predetermined signals for a match; (2) identify the movement from the sensors 105 as falling into a class of movements based on the predetermined signals, (3) determine one or more parameters associated with the movement; (4) transmit an indicator to one or more filters of the relevant parameter; (5) activate one or more filters based on the one or more parameters; and/or (6) log or store the activity levels in the sensor manager 109's memory such as a flash memory of the sensors 105. This decreases the amount of data transferred to the UE 101 and to the corresponding service, thereby extending both the sensors 105's and the UE 101's operational capacities (e.g., battery lives) while also removing potentially noisy data (e.g., motion artifacts) from the data set. In one embodiment, the sensor manager processes the context information to recognize simple and/or coarse-grained daily activities (e.g., sitting, standing, walking, etc.) to optimize the energy consumption of the sensors 105 and speed filter adaptation.

It is noted that although various embodiments discuss context information as motion or movement information, it is contemplated that the context information may relate to any operational parameter corresponding to the sensors 105 performing the data collection. For example, if data collecting sensors 105 are ECG sensors, the context information may also include parameters related to oxygenation levels in the blood, heart rate, galvanic skin response, or a combination of the parameters.

By way of example, the communication network 111 of system 100 includes one or more networks such as a data network (not shown), a wireless network (not shown), a telephony network (not shown), or any combination thereof. It is contemplated that the data network may be any local area network (LAN), metropolitan area network (MAN), wide area network (WAN), a public data network (e.g., the Internet), short range wireless network, or any other suitable packet-switched network, such as a commercially owned, proprietary packet-switched network, e.g., a proprietary cable or fiber-optic network, and the like, or any combination thereof. In addition, the wireless network may be, for example, a cellular network and may employ various technologies including enhanced data rates for global evolution (EDGE), general packet radio service (GPRS), global system for mobile communications (GSM), Internet protocol multimedia subsystem (IMS), universal mobile telecommunications system (UMTS), etc., as well as any other suitable wireless medium, e.g., worldwide interoperability for microwave access (WiMAX), Long Term Evolution (LTE) networks, code division multiple access (CDMA), wideband code division multiple access (WCDMA), wireless fidelity (WI-FI), wireless LAN (WLAN), Bluetooth®, Internet Protocol (IP) data casting, satellite, mobile ad-hoc network (MANET), and the like, or any combination thereof.

The UE 101 is any type of mobile terminal, fixed terminal, or portable terminal including a mobile handset, station, unit, device, multimedia computer, multimedia tablet, Internet node, communicator, desktop computer, laptop computer, notebook computer, netbook computer, tablet computer, personal communication system (PCS) device, personal navigation device, personal digital assistants (PDAs), audio/video player, digital camera/camcorder, positioning device, television receiver, radio broadcast receiver, electronic book device, game device, or any combination thereof, including the accessories and peripherals of these devices, or any combination thereof. It is also contemplated that the UE 101 can support any type of interface to the user (such as "wearable" circuitry, etc.).

By way of example, the UE 101, the sensor group 103, the sensors 105, the application 107, and service platform 113 communicate with each other and other components of the communication network 111 using well known, new or still developing protocols. In this context, a protocol includes a set of rules defining how the network nodes within the communication network 111 interact with each other based on information sent over the communication links. The protocols are effective at different layers of operation within each node, from generating and receiving physical signals of various types, to selecting a link for transferring those signals, to the format of information indicated by those signals, to identifying which software application executing on a computer system sends or receives the information. The conceptually different layers of protocols for exchanging information over a network are described in the Open Systems Interconnection (OSI) Reference Model.

Communications between the network nodes are typically effected by exchanging discrete packets of data. Each packet typically comprises (1) header information associated with a particular protocol, and (2) payload information that follows the header information and contains information that may be processed independently of that particular protocol. In some protocols, the packet includes (3) trailer information following the payload and indicating the end of the payload information. The header includes information such as the source of the packet, its destination, the length of the payload, and other properties used by the protocol. Often, the data in the payload for the particular protocol includes a header and payload for a different protocol associated with a different, higher layer of the OSI Reference Model. The header for a particular protocol typically indicates a type for the next protocol contained in its payload. The higher layer protocol is said to be encapsulated in the lower layer protocol. The headers included in a packet traversing multiple heterogeneous networks, such as the Internet, typically include a physical (layer 1) header, a data-link (layer 2) header, an internetwork (layer 3) header and a transport (layer 4) header, and various application headers (layer 5, layer 6 and layer 7) as defined by the OSI Reference Model.

In one embodiment, the application 107 and the service platform 113 may interact according to a client-server model. According to the client-server model, a client process sends a message including a request to a server process, and the server process responds by providing a service (e.g., providing map information). The server process may also return a message with a response to the client process. Often the client process and server process execute on different computer devices, called hosts, and communicate via a network using one or more protocols for network communications. The term "server" is conventionally used to refer to the process that provides the service, or the host computer on which the process operates. Similarly, the term "client" is conventionally used to refer to the process that makes the request, or the host computer on which the process operates. As used herein, the terms "client" and "server" refer to the processes, rather than the host computers, unless otherwise clear from the context. In addition, the process performed by a server can be broken up to run as multiple processes on multiple hosts (sometimes called tiers) for reasons that include reliability, scalability, and redundancy, among others.

Figure 2:
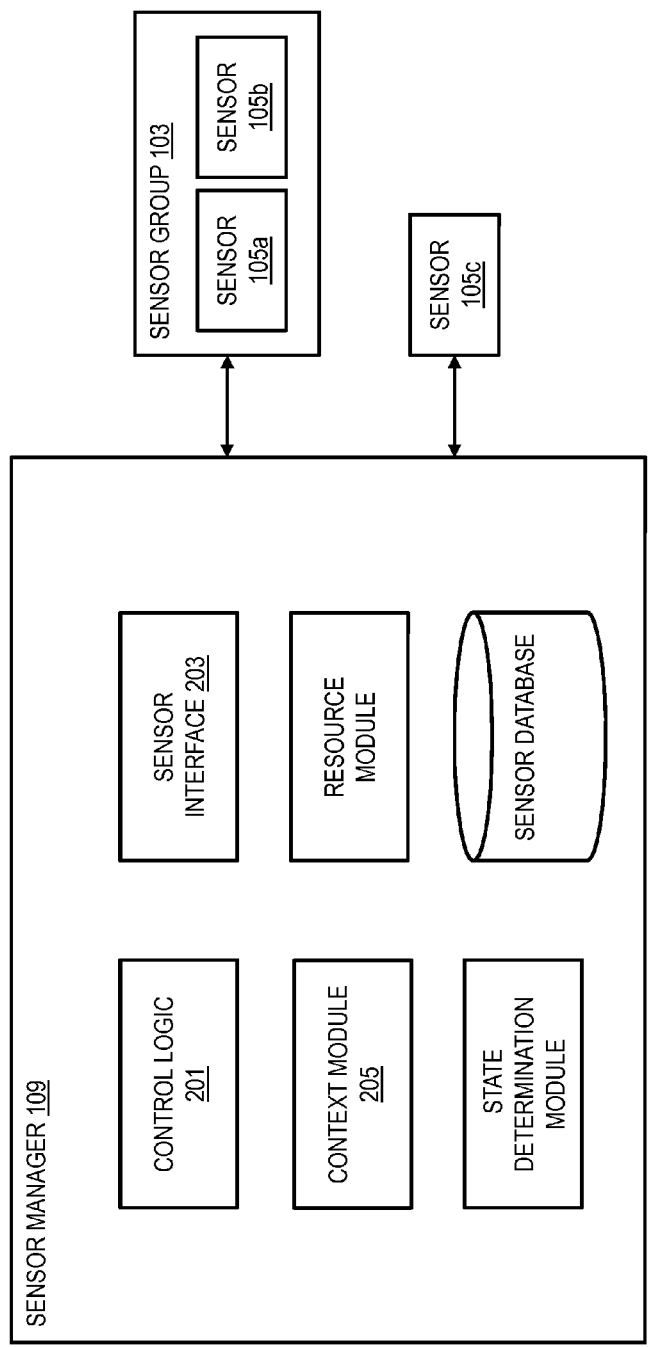
FIG. 2 is a diagram of the components of a sensor and filter manager, according to one embodiment.

FIG. 2 is a diagram of the components of a sensor manager, according to one embodiment. By way of example, the sensor manager 109 includes one or more components for providing adaptive display and filtering of sensors and sensor data. It is contemplated that the functions of these components may be combined in one or more components or performed by other components of equivalent functionality. In this embodiment, the sensor manager 109 includes at least a control logic 201 which executes at least one algorithm for executing functions of the sensor manager 109. In one embodiment, the control logic 201 interacts with a sensor interface 203 to receive or otherwise detect context information and/or data collected by one or more sensors 105. In one embodiment, the sensor interface is based on short range radio technology (e.g., BLUETOOTH wireless technology standard, WI-FI local area wireless networking technology, ANT/ANT+ powered nodes/interoperable wireless transfer capability, ZIGBEE wireless network standard, etc.).

The context module 205 receives, stores in Sensor Database 209, and/or processes context information received via the sensor interface 203. By way of example, the context module 205 processes the context information to determine one or more operational parameters of the sensors 105 that are to collect data. In one embodiment, the context module 205 can extract the operational parameters or other features from context information or context information stream. By way of example, features may be extracted according to time and/or frequency domains of the features that can distinguish activity levels and/or classify the levels into specific activities (e.g., walking, sitting, running, etc.) using Response Module 207 and State Determination Module 211. In some embodiments, where resources (e.g., processing resources or power) are limited (e.g., in the sensors 105 or the UE 101), just the time domain may be investigated. Under this scenario, a feature vector is calculated within a predetermined time window (e.g., five seconds) with a certain overlap between the windows (e.g., 50% overlap).

Figure 3:
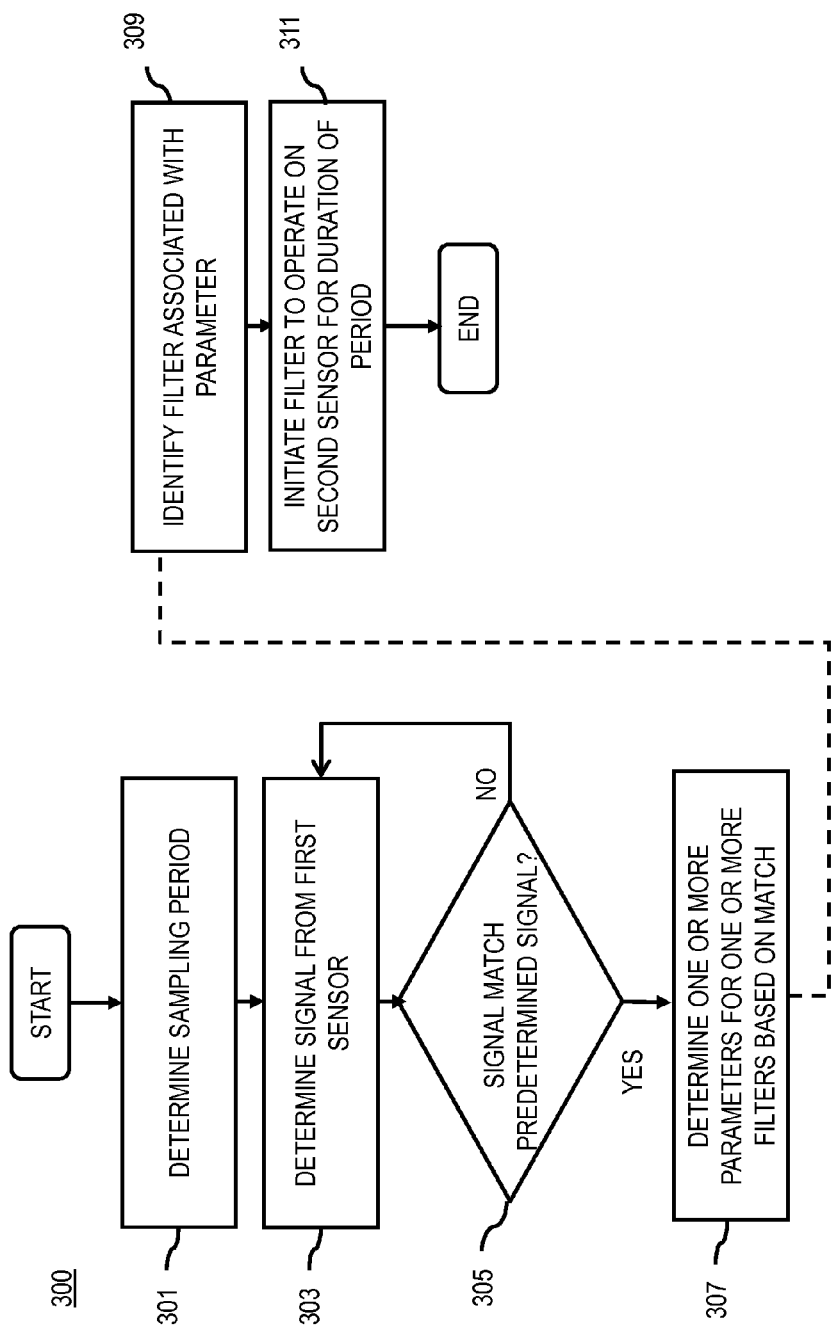
FIG. 3 is a flowchart of a process for providing adaptive display and filtering of sensor data, according to one embodiment.

FIG. 3 is a flowchart of a process for providing adaptive display and filtering of sensor data, according to one embodiment. In one embodiment, the sensor manager 109 performs the process 300 and is implemented in, for instance, a chip set including a processor and a memory as shown FIG. 10. The process 300 provides a general overall process for providing adaptive display and filtering of sensors and sensor data. In step 301, the sensor manager 109 may determine a beginning of a sampling period for one or more sensors 105. Upon initiation of a sampling period, the sensor manager 109 may begin determination of one or more signals from one or more sensors 105, where the one or more sensors 105 are associated with determining at least one operational state of one or more other sensors (step 303). The operational states of the sensors 105 may include setting and/or modifying related operational parameters including sampling rate, parameters to sample, transmission protocol, activity timing, etc.

Next, the sensor manager 109 may process and/or facilitate processing to compare the one or more signals against one or more predetermined signals (step 305). Should the one or more signals correspond to one or more predetermined signals, further processing towards triggering the associated adaptive display and filtering may ensue. If the one or more signals do not appear to match with one or more predetermined signals, monitoring of the one or more signals may continue until a match occurs between the signals from sensors 105 and one or more predetermined signals. In one embodiment, the sensor manager 109 may monitor and/or determine of the beginning of a sampling period of the one or more signals periodically, continuously, according to a schedule, on demand, or a combination thereof.

In step 305, the sensor manager 109 may apply adaptive display and filtering based, at least in part, on a first sensor 105 (e.g., an accelerometer). In one embodiment, the context information is further based, at least in part, on at least a third sensor 105, one or more other sensors 105 or a combination thereof. It is contemplated that the first sensor 105, the third sensor 105, and/or other sensors 105 may provide information on the operational state related to one or more operational parameters of the second sensor 105. In one embodiment, the second sensor 105 is a wearable health or wellness sensor. In yet another embodiment, the second sensor 105 (e.g., a physiological sensor) is affected by movement, and the first sensor 105 (e.g., an accelerometer) detects at least one movement or one or more characteristics of the at least one movement of the second sensor. Similar to the first sensor 105, the second sensor can be associated with one or more other sensors 105 that are responsible for collecting a set of data. For example, the second sensor 105 (e.g., an ECG sensor) can be combined with other sensors 105 (e.g., PPG sensor, GSR sensor, etc.) so that a suite of parameters can be sampled concurrently and controlled by the context information of a first set of sensors.

Should the comparison between one or more signals from sensors 105 yield a match with one or more predetermined signals, the sensor manager 109 may determine one or more parameters for one or more filters based, at least in part, on the comparison (step 307). One or more parameters may be associated with one or more predetermined signals. Therefore, when one or more signals from sensors 105 matches one or more predetermined signals, the sensor manager 109 may determine one or more parameters relevant to the user state, based on the predetermined signals and their associated parameters. The one or more parameters triggered, are then the parameters associated with the one or more predetermined signals that match the user state of the sampling period (as given by the one or more signals from sensors 105).

Once one or more parameters associated with the predetermined signal are determined, the sensor manager 109 may employ the one or more parameters to act on one or more filters associated with the one or more parameters (step 309). The associated one or more filters may then operate on the one or more sensors, one or more other signals determined from the one or more other sensors, or a combination thereof (step 311), thus applying a filtering algorithm that is tailored to the specific incoming signal. By applying a filter in accordance with the predetermined signal or model, relevant filtering may be employed without a long period of sampling to the appropriate filtering. In other words, filtering is adapted upon identifying the incoming signal with parameters associated with its matching predetermined signals, thus eliminating the need for long sampling before proper filtering may be determined and adopted.

In one embodiment, matching in step 305 as well as subsequent processing in steps 307 and 309 may be based on a classification system. For instance, where there is a match between one or more incoming signals and predetermined signals, the sensor manager 109 may process the one or more signals, one or more predetermined signals, or combination thereof into classes. In fact, the match or comparison between incoming and predetermined signal is based, at least in part, on the classes. A possible form of classification may be: movement states. In one possible execution of step 307, the sensor manager 109 may process and/or facilitate processing of the one or more signals to determine one or more movement states for the sampling period and determine one or more parameters based on the one or more movement states. For example, one or more predetermined signals may be classified as the movement state, "walking." If the one or more signals from the sensors 105 are found similar to one or more predetermined signals in "walking," the one or more signals from the sensors may be classified as falling into "walking" The sensor manager 109 may then infer that the user is walking, or, in walking state. From there, the sensor manager 109 may determine one or more parameters associated with the "walking" class. In step 309 for such an embodiment, the one or more parameters may then prompt or cause to prompt one or more filters or filtering algorithms associated with "walking" to operate on the one or more sensors 105, signals from one or more other sensors 105, or a combination thereof.

In a further embodiment, the sensor manager 109 may determine one or more updates to the movement states may be based, at least in part, on monitoring of one or more signals from sensors 105 that is periodic, continuous, according to a schedule, on demand, or a combination thereof. For instance, one sampling period may show the user to be in a "walking" state, subsequently triggering the one or more parameters associated with "walking," thus prompting the initiation of one or more filters for filtering one or more signals produced by "walking" state (as associated with the one or more parameters). Monitoring of the signals may show a shift from movement state signals to increased activity, whereupon the sensor manager 109 may update the movement state to "running" By extension, the one or more parameters associated with the movement state and its filtering may update according to the change in activity. In this example, the one or more parameters associated with "running" may then displace the "walking" parameters. Furthermore, the one or more parameters associated with "running" may then act on filters associated with "running" to fit the new movement state.

In another further embodiment, the sensor manager 109 may process and/or facilitate processing of the one or more predetermined signals to generate one or more models, wherein the comparison of the one or more signals against the one or more predetermined signals is based, at least in part on the one or more models. In such a process, the sensor manager 109 may aggregate input from different sensors to generate the models. In one scenario, the sensors may provide sampling of various types of data. Such a form of modeling may provide more general or comprehensive application of adaptive display and filtering or supply adaptation for a wider variety of user applications.

Figure 4:
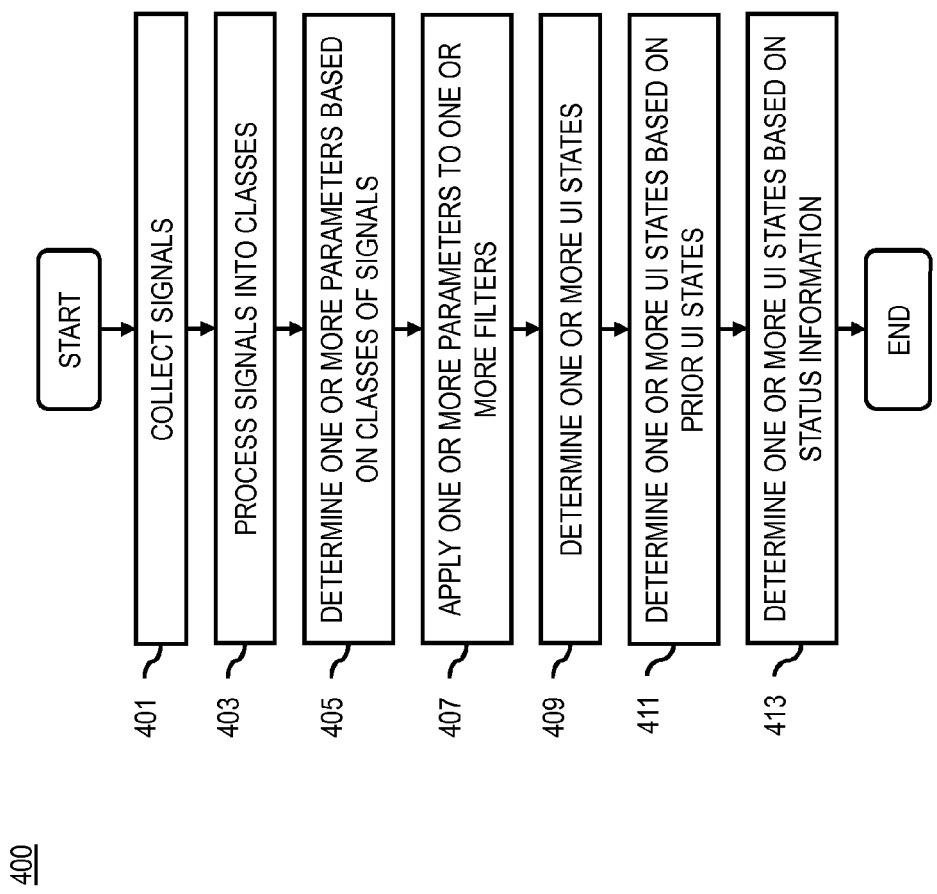
FIG. 4 is a flowchart of a process for establishing parameters to enable adaptive display and filtering, according to one embodiment.

FIG. 4 is a flowchart of a process for establishing parameters to enable adaptive display and filtering, according to one embodiment. FIG. 4 provides one example of the means to create the models underlying the model-based adaptation detailed in FIG. 3. To start, the sensor manager 109 may collect samples as described previously via one or more sensors 105 (step 401). Next, the sensor manager 109 may process and/or facilitate processing of the signals to determine one or more parameters. In one embodiment, the sensor manager 109 may process and/or facilitate processing of the one or more predetermined signals to determine one or more parameters based on classes. In such a scenario, the one or more parameters may be associated with one or more predetermined signals as grouped into one or more classes. Such a case may include sorting the collected sample signals into one or more classes (step 403). The sensor manager may then analyze the one or more classes to find one or more parameters derived from the signals in the particular classes (step 405). In one embodiment, the one or more parameters determined by analyzing a class of signals may pertain to initiation data, coefficients determined from the initiation data, or a combination thereof. The one or more parameters are associated with the class of predetermined signals such that identifying a class of predetermined signal permits the sensor manager 109 to also pinpoint one or more parameters for one or more filters specific to the identified class.

Optionally in a further embodiment, the one or more parameters may be associated with one or more filters (step 407). As such, one or more filters may be made to correspond to particular signals. For example, in the scenario where collected signals are sorted into one or more classes, one or more parameters are associated with the one or more classes and the one or more parameters are in turn associated with one or more filters, the one or more filters correspond to one or more specific classes of signals. In this way, filtering specific to incoming signal may be applied upon identification of one or more incoming signal matching predetermined signals. Such a method permits adaptation to the incoming signal without a relatively long sampling, "learning" period.

At step 409, the sensor manager 109 may process and/or facilitate a processing of the one more signals for determining one or more UI states for presenting one or more sensor data at a device, at the one or more sensors, or a combination thereof. For example, the UI states may include an idle mode (e.g., display off), a data display mode (e.g., display on), device status mode (e.g., battery status), displaying other data and information mode, and the like. In one embodiment, the display mode may be based, at least in part, on a timer that may be configured by one or more applications, modules, sensors, users, service providers, and the like.

At step 411, the sensor manager 109 determines the one or more user interface states based, at least in part, on one or more prior user interface states, one or more user preferences, one or more configurations of one or more devices, or a combination thereof. For example, if a prior UI state is known (e.g., has been saved), then a user may interact with the display device; for instance, by one or more taps, touch points, gestures, and the like, to change from one mode to a prior mode (e.g., from idle mode to the saved mode.) Further, the display mode may be determined by one or more user preferences at a device, at a service provider, and/or one or more configurations of a device, for example, according to device/user activities, time of day, one or more service provider triggers, and the like.

At step 413, the sensor manager 109 determines the one or user interface states based, at least in part, on one or more status information items associated with the one or more devices, one or more user interactions, or a combination thereof. For example, one or more sensor data may indicate one or more information items, statistics, parameters, and the like that may be of interest to the user and should be displayed at one or more devices.

Figure 5:
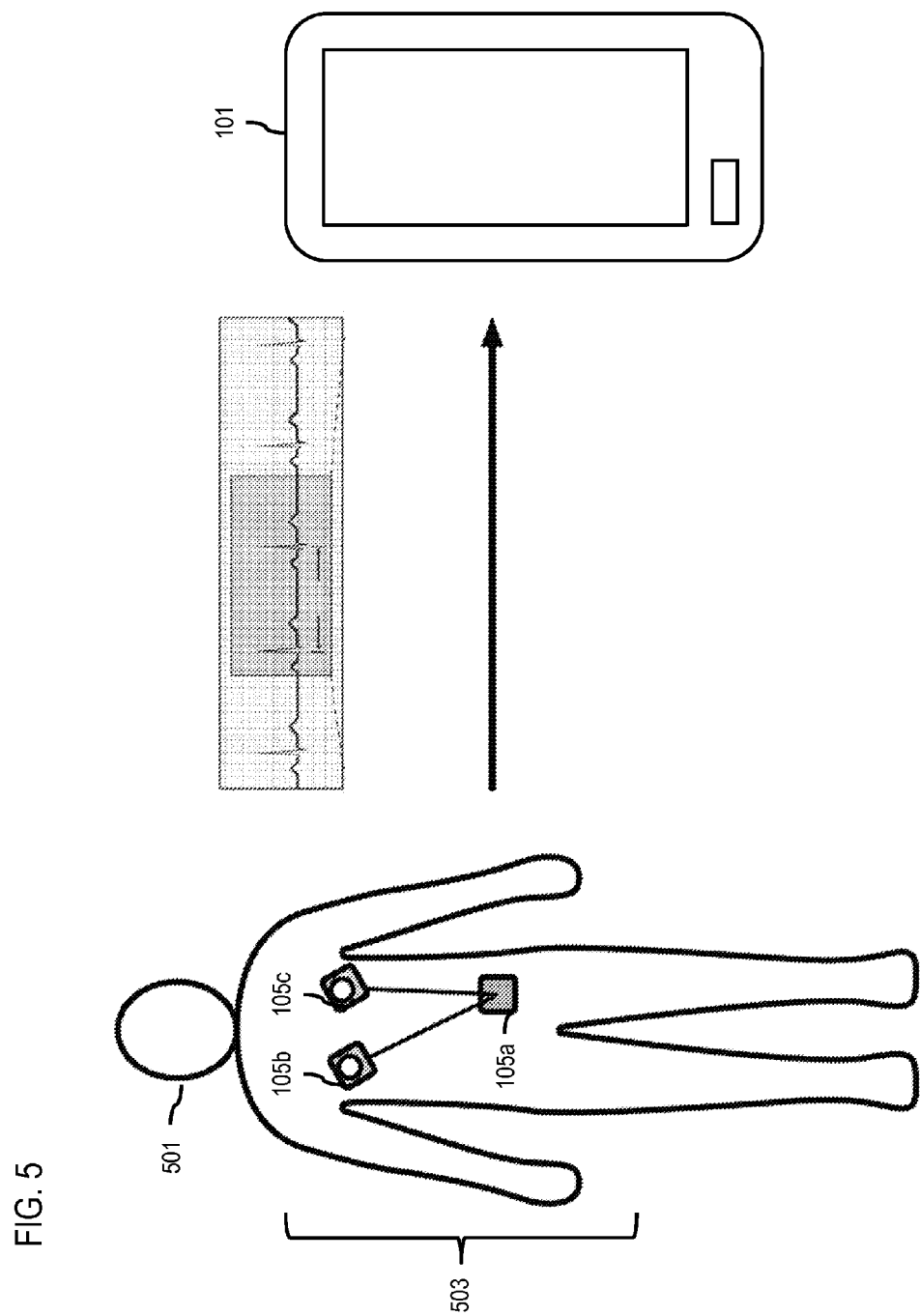
FIG. 5 is a diagram of a framework for adaptive display and filtering of health and wellness sensors, according to one embodiment.

FIG. 5 is a diagram of a framework for adaptive display and filtering of health and wellness sensors, according to one embodiment. As shown, a user 501 is equipped with a wearable sensor system 503 (e.g., a BSN) consisting of three sensors 105*a*-105*c*. In this example, the sensors 105*b* and 105*c* have connectivity to a sensor 105*a* which is responsible for collecting and transmitting continuous or substantially continuous monitoring data the UE 101. More specifically, the sensors 105*a*-105*c* include at least an accelerometer for determining context information and an ECG sensor 105 which is operated based on the context information according to the various embodiments described herein. The sensors 105*a*-105*c* stream the ECG signals 505 to the mobile device for processing, storage, and/or classification.

Figure 6:
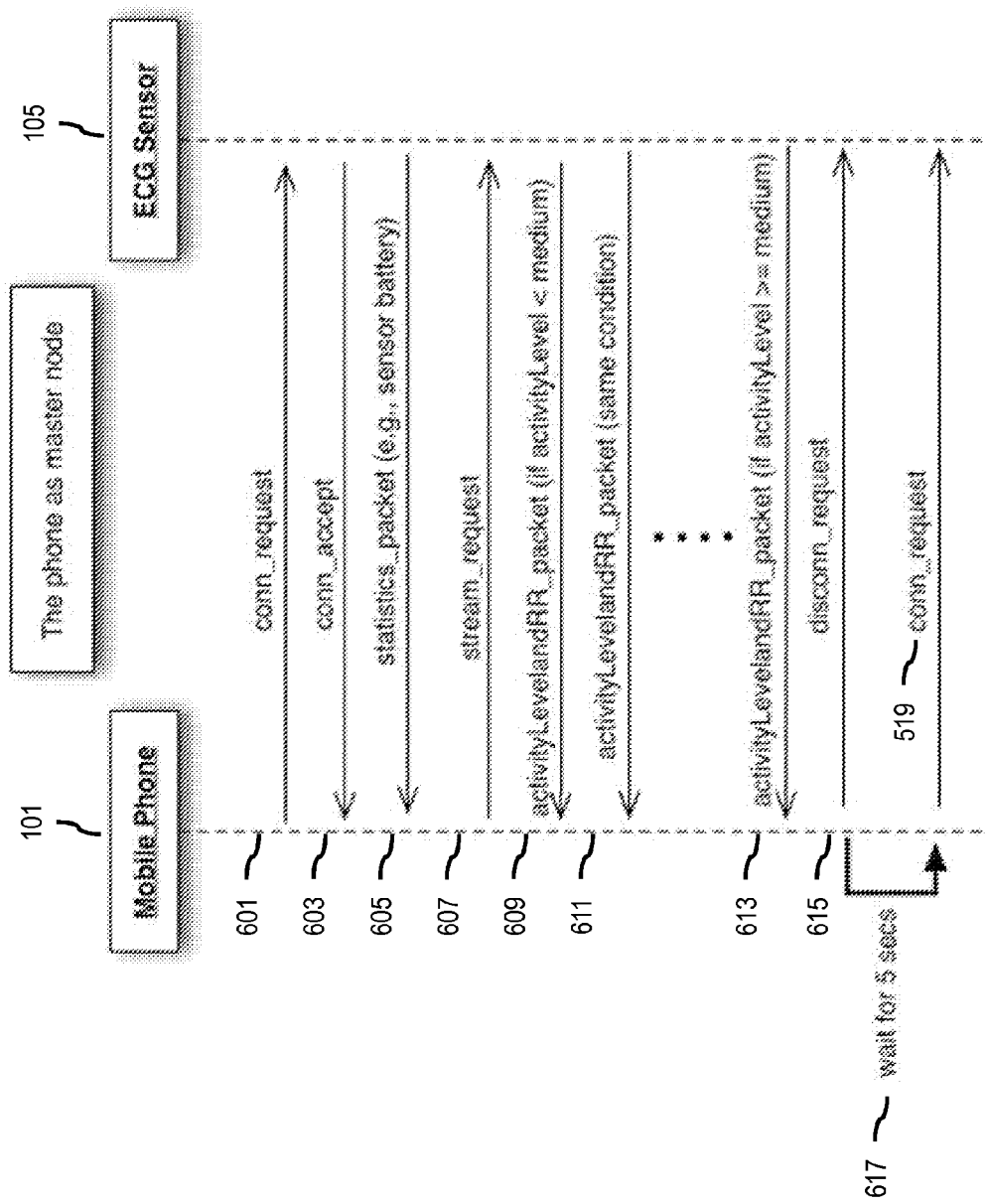
FIG. 6 is a diagram of a process for adaptive display and filtering of sensors and sensor data wherein a device acts as a master of the process, according to various embodiments.

FIG. 6 is a diagram of a process for adaptive display and filtering of sensors and sensor data wherein a device acts as a master of the process, according to various embodiments. FIG. 6 presents a scenario where the UE 101 is acting as a master (e.g., in a Bluetooth Personal Area Network) with respect to communication with a sensor 105. More specifically, FIG. 6 is a time sequence diagram illustrating the communication protocol between the UE 101 and the ECG sensor. At 601, the mobile phone or UE 101 sends a connection request (e.g., a Bluetooth connection request) to the ECG sensor 105. The ECG sensor 105 responds with an acceptance message 603 and also transmits a statistics data package including, for instance, resource consumption and availability information (e.g., sensor battery level) of the ECG sensor 105 (step 605).

In response, the UE 101 sends a request to the ECG sensor 105 to begin streaming sensor data (step 607). At 609, the ECG sensor 105 determines that the activity level (or movement state) of the monitor subject, which implicates one or more parameters associated with that activity level (e.g. a medium level). At 611, the ECG sensor 105 continues to stream the data based on the activity level. Alternatively, the ECG sensor 105 can buffer the data and then send the data in batches rather as a continuous stream.

At 613, the ECG sensor 105 detects that the activity level has increased above the level, perhaps no longer matches one or more predetermined signals, and informs the UE 101. In response, the UE 101 sends a disconnection request to the ECG sensor 105 so that the data streaming and/or data collection can stop until the activity level matches one or more predetermined signals (step 615). The UE 101 sets a timer for a predetermined length (e.g., 5 seconds) (step 617) before initiating another connection request to resume the ECG data stream (step 619). If the activity level still does not match one or more predetermined lengths, the UE 101 resets the timer and waits another 5 seconds. Otherwise, the ECG data stream resumes.

Figure 7:
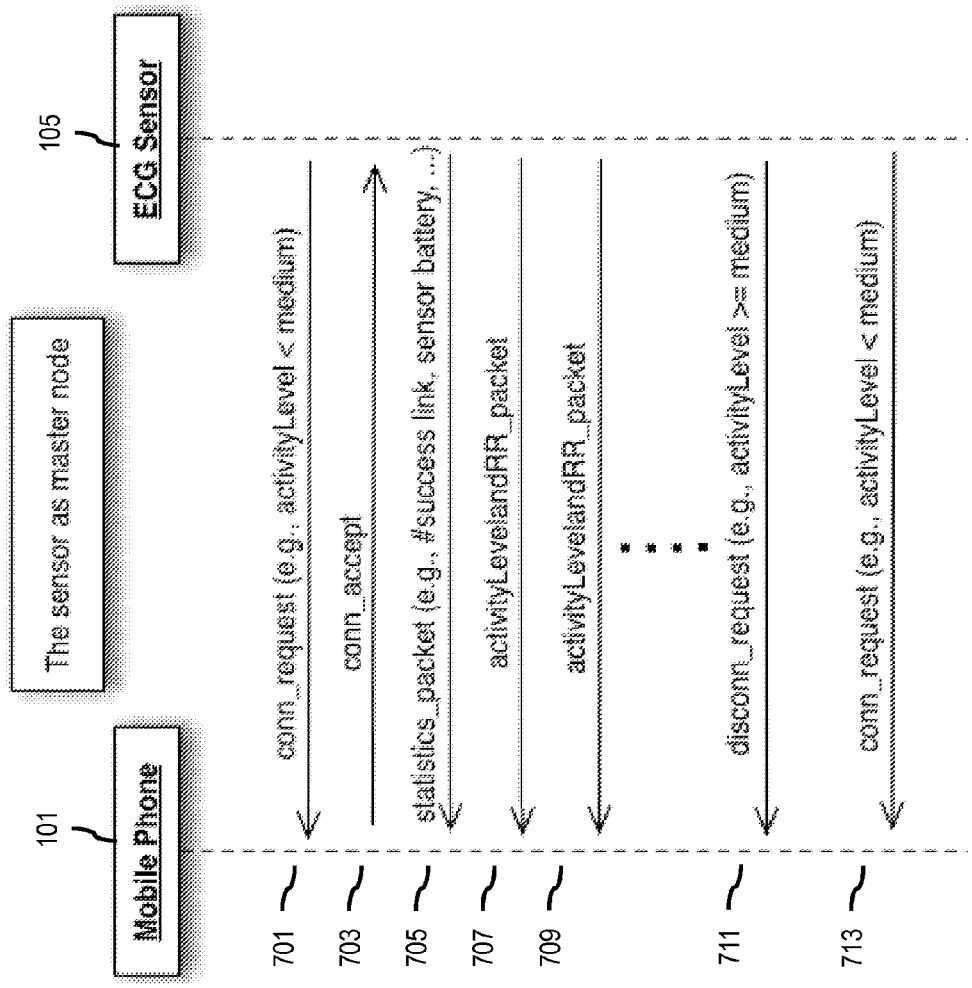
FIG. 7 is a diagram of a process for adaptive display and filtering of sensors and sensor data wherein a sensor acts as a master of the process, according to various embodiments.

FIG. 7 is a diagram of a process for adaptive display and filtering of sensors and sensor data wherein a device acts as a master of the process, according to various embodiments. The scenario of FIG. 7 is similar to that presented in FIG. 6 with the exception that the ECG sensor 105 is acting as a master of the communication session instead of the UE 101. In other words, the sensor 105 controls the wireless connection between it and the UE 101. An advantage of this approach is that the sensor does not need to consume power listening for the incoming connection request from the UE 101. Moreover, the ECG sensor 105 can control the connection depending on its accelerometer or other sensor reading.

FIG. 7 is a time sequence diagram illustrating the communication protocol between the UE 101 and the ECG sensor. At 701, the ECG sensor 105 sends a connection request to the UE 101. The UE 101 accepts the connection (step 703) and the ECG sensor 105 begins by sending statistics packets to the UE 101 (step 705). As discussed above, the statistics packets may contain information about resource consumption or availability as well as statistics on the quality of the connection. At 707 and 709, the ECG sensor 105 begins streaming the ECG data as long as the sensor 105 determines that the activity level matches a predetermined signal. At 711, the activity level ceases to match predetermined signals and the ECG sensor 105 sends a disconnection request to the UE 101. When the activity level matches a predetermined signal again, the ECG sensor 105 sends a connection request to resume the streaming of the ECG data to the UE 101 (step 713).

Figure 8:
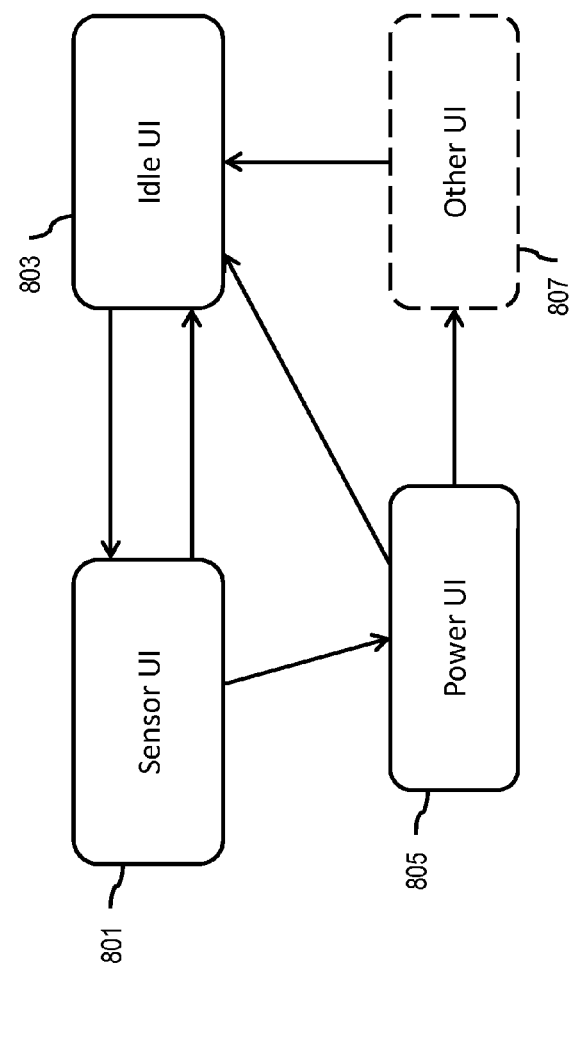
FIG. 8 illustrates various user interface states for displaying sensor data, according to various embodiments.

FIG. 8 illustrates various user interface states for displaying sensor data, according to various embodiments. FIG. 8 shows UI flow process 800 where one or more displays at one or more sensors and/or devices may be utilized for displaying/presenting various data and information items at various times. Further, the UI visible at one or more devices and/or sensors may be configured by a user via one or more of the one or more devices, for example, to switch states based, at least in part, on one or more triggers and/or interactions by a user.

In one embodiment, information and/or a prior UI state may be saved for future reference/return. In one embodiment, at 801, a sensor and/or a device may present/display sensor information at a display, wherein the presentation on the display may be triggered and/or may be based, at least in part, on a predetermined time interval (e.g., every 15, 30, 45, etc. seconds), which may be configured by a user, by one or more applications, one or more service providers, one or more devices, and the like. In one embodiment, at 801, once the presentation at the display is completed and/or a trigger condition is determined (e.g., a predetermined timer expires), the UI state may switch to idle state 803 where the display device may be set to a state (e.g., turned off) for energy conservation. In one embodiment, a user and/or an application may cause (e.g., tap, touch, trigger condition, etc.) for the display state to switch from 801 to a power UI state 805 where power information (e.g., battery condition, energy consumption, etc.) associated with one or more sensors and/or devices may be presented. In one embodiment, the UI state information may be saved and the UI state may switch to the idle state 803 or a user and/or an application may cause the UI state to switch to one or more other UI states 807 that may be available at a sensor and/or at a device. Similarly, the one or more other UI states 807 may switch to the idle state 803 upon, for example, expiration of a timer, trigger by a user, or an application, or a service provider, and the like. In various embodiments, a user interaction and/or a trigger condition at the idle state 803 may cause the UI state to switch to a last saved UI state (e.g., power UI state, other UI state, etc.) otherwise, the UI state may switch to the sensor UI state 801.

The processes described herein for providing adaptive display and filtering of sensors and sensor data may be advantageously implemented via software, hardware, firmware or a combination of software and/or firmware and/or hardware. For example, the processes described herein, may be advantageously implemented via processor(s), Digital Signal Processing (DSP) chip, an Application Specific Integrated Circuit (ASIC), Field Programmable Gate Arrays (FPGAs), etc. Such exemplary hardware for performing the described functions is detailed below.

Figure 9:
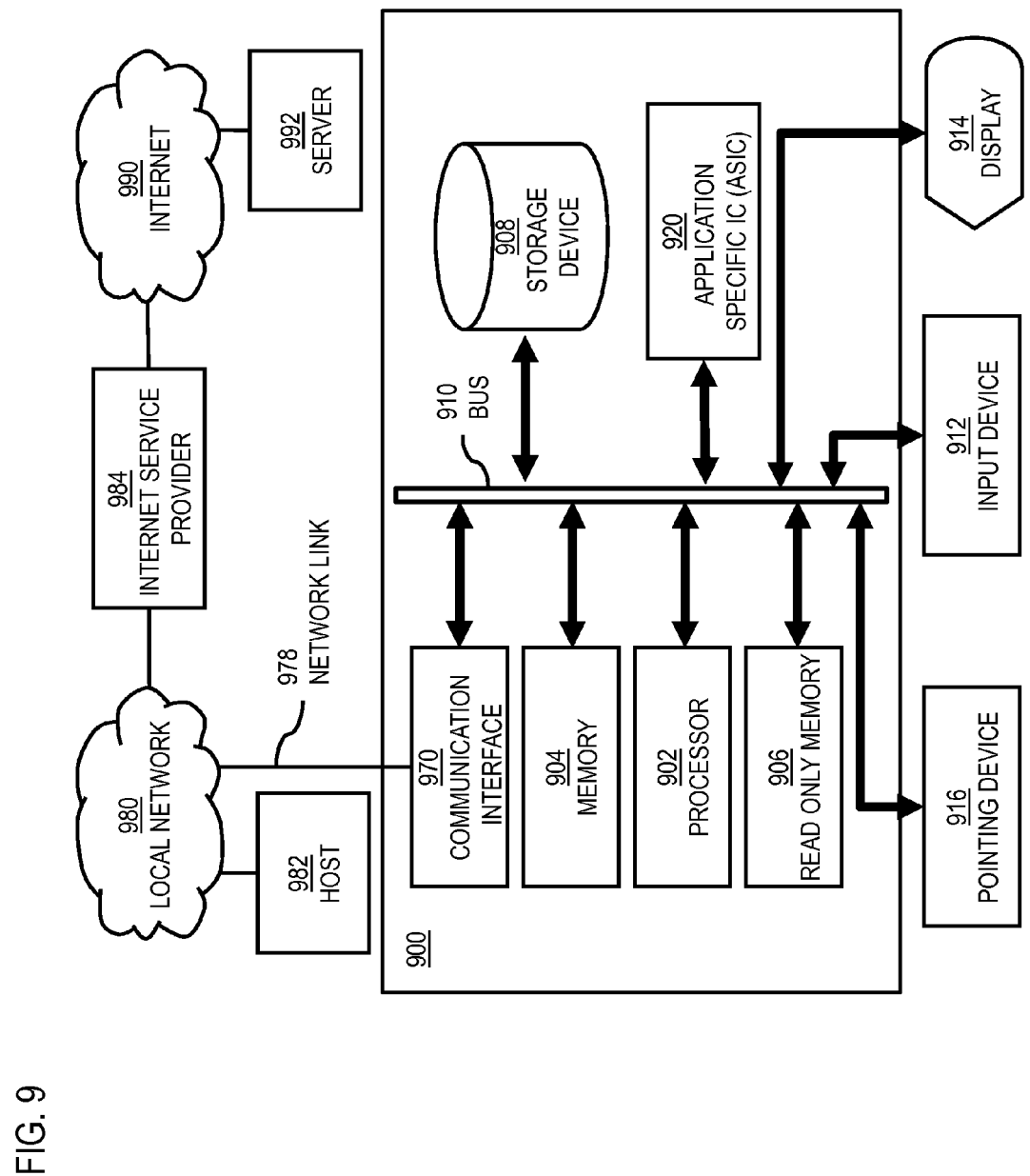
FIG. 9 is a diagram of hardware that can be used to implement an embodiment of the invention.

FIG. 9 illustrates a computer system 900 upon which an embodiment of the invention may be implemented. Although computer system 900 is depicted with respect to a particular device or equipment, it is contemplated that other devices or equipment (e.g., network elements, servers, etc.) within FIG. 9 can deploy the illustrated hardware and components of system 900. Computer system 900 is programmed (e.g., via computer program code or instructions) to provide adaptive display and filtering of sensors and sensor data as described herein and includes a communication mechanism such as a bus 910 for passing information between other internal and external components of the computer system 900. Information (also called data) is represented as a physical expression of a measurable phenomenon, typically electric voltages, but including, in other embodiments, such phenomena as magnetic, electromagnetic, pressure, chemical, biological, molecular, atomic, sub-atomic and quantum interactions. For example, north and south magnetic fields, or a zero and non-zero electric voltage, represent two states (0, 1) of a binary digit (bit). Other phenomena can represent digits of a higher base. A superposition of multiple simultaneous quantum states before measurement represents a quantum bit (qubit). A sequence of one or more digits constitutes digital data that is used to represent a number or code for a character. In some embodiments, information called analog data is represented by a near continuum of measurable values within a particular range. Computer system 900, or a portion thereof, constitutes a means for performing one or more steps of providing adaptive display and filtering of sensors and sensor data.

A bus 910 includes one or more parallel conductors of information so that information is transferred quickly among devices coupled to the bus 910. One or more processors 902 for processing information are coupled with the bus 910.

A processor (or multiple processors) 902 performs a set of operations on information as specified by computer program code related to providing adaptive display and filtering of sensors and sensor data. The computer program code is a set of instructions or statements providing instructions for the operation of the processor and/or the computer system to perform specified functions. The code, for example, may be written in a computer programming language that is compiled into a native instruction set of the processor. The code may also be written directly using the native instruction set (e.g., machine language). The set of operations include bringing information in from the bus 910 and placing information on the bus 910. The set of operations also typically include comparing two or more units of information, shifting positions of units of information, and combining two or more units of information, such as by addition or multiplication or logical operations like OR, exclusive OR (XOR), and AND. Each operation of the set of operations that can be performed by the processor is represented to the processor by information called instructions, such as an operation code of one or more digits. A sequence of operations to be executed by the processor 902, such as a sequence of operation codes, constitute processor instructions, also called computer system instructions or, simply, computer instructions. Processors may be implemented as mechanical, electrical, magnetic, optical, chemical or quantum components, among others, alone or in combination.

Computer system 900 also includes a memory 904 coupled to bus 910. The memory 904, such as a random access memory (RAM) or any other dynamic storage device, stores information including processor instructions for providing adaptive display and filtering of sensors and sensor data. Dynamic memory allows information stored therein to be changed by the computer system 900. RAM allows a unit of information stored at a location called a memory address to be stored and retrieved independently of information at neighboring addresses. The memory 904 is also used by the processor 902 to store temporary values during execution of processor instructions. The computer system 900 also includes a read only memory (ROM) 906 or any other static storage device coupled to the bus 910 for storing static information, including instructions, that is not changed by the computer system 900. Some memory is composed of volatile storage that loses the information stored thereon when power is lost. Also coupled to bus 910 is a non-volatile (persistent) storage device 908, such as a magnetic disk, optical disk or flash card, for storing information, including instructions, that persists even when the computer system 900 is turned off or otherwise loses power.

Information, including instructions for providing adaptive display and filtering of sensors and sensor data, is provided to the bus 910 for use by the processor from an external input device 912, such as a keyboard containing alphanumeric keys operated by a human user, or a sensor. A sensor detects conditions in its vicinity and transforms those detections into physical expression compatible with the measurable phenomenon used to represent information in computer system 900. Other external devices coupled to bus 910, used primarily for interacting with humans, include a display device 914, such as a cathode ray tube (CRT), a liquid crystal display (LCD), a light emitting diode (LED) display, an organic LED (OLED) display, a plasma screen, or a printer for presenting text or images, and a pointing device 916, such as a mouse, a trackball, cursor direction keys, or a motion sensor, for controlling a position of a small cursor image presented on the display 914 and issuing commands associated with graphical elements presented on the display 914. In some embodiments, for example, in embodiments in which the computer system 900 performs all functions automatically without human input, one or more of external input device 912, display device 914 and pointing device 916 is omitted.

In the illustrated embodiment, special purpose hardware, such as an application specific integrated circuit (ASIC) 920, is coupled to bus 910. The special purpose hardware is configured to perform operations not performed by processor 902 quickly enough for special purposes. Examples of ASICs include graphics accelerator cards for generating images for display 914, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 900 also includes one or more instances of a communications interface 970 coupled to bus 910. Communication interface 970 provides a one-way or two-way communication coupling to a variety of external devices that operate with their own processors, such as printers, scanners and external disks. In general the coupling is with a network link 978 that is connected to a local network 980 to which a variety of external devices with their own processors are connected. For example, communication interface 970 may be a parallel port or a serial port or a universal serial bus (USB) port on a personal computer. In some embodiments, communications interface 970 is an integrated services digital network (ISDN) card or a digital subscriber line (DSL) card or a telephone modem that provides an information communication connection to a corresponding type of telephone line. In some embodiments, a communication interface 970 is a cable modem that converts signals on bus 910 into signals for a communication connection over a coaxial cable or into optical signals for a communication connection over a fiber optic cable. As another example, communications interface 970 may be a local area network (LAN) card to provide a data communication connection to a compatible LAN, such as Ethernet. Wireless links may also be implemented. For wireless links, the communications interface 970 sends or receives or both sends and receives electrical, acoustic or electromagnetic signals, including infrared and optical signals, that carry information streams, such as digital data. For example, in wireless handheld devices, such as mobile telephones like cell phones, the communications interface 970 includes a radio band electromagnetic transmitter and receiver called a radio transceiver. In certain embodiments, the communications interface 970 enables connection to the communication network 111 for providing adaptive display and filtering of sensors and sensor data.

The term "computer-readable medium" as used herein refers to any medium that participates in providing information to processor 902, including instructions for execution. Such a medium may take many forms, including, but not limited to computer-readable storage medium (e.g., non-volatile media, volatile media), and transmission media. Non-transitory media, such as non-volatile media, include, for example, optical or magnetic disks, such as storage device 908. Volatile media include, for example, dynamic memory 904. Transmission media include, for example, twisted pair cables, coaxial cables, copper wire, fiber optic cables, and carrier waves that travel through space without wires or cables, such as acoustic waves and electromagnetic waves, including radio, optical and infrared waves. Signals include man-made transient variations in amplitude, frequency, phase, polarization or other physical properties transmitted through the transmission media. Common forms of computer-readable media include, for example, a floppy disk, a flexible disk, hard disk, magnetic tape, any other magnetic medium, a CD-ROM, CDRW, DVD, any other optical medium, punch cards, paper tape, optical mark sheets, any other physical medium with patterns of holes or other optically recognizable indicia, a RAM, a PROM, an EPROM, a FLASH-EPROM, an EEPROM, a flash memory, any other memory chip or cartridge, a carrier wave, or any other medium from which a computer can read. The term computer-readable storage medium is used herein to refer to any computer-readable medium except transmission media.

Logic encoded in one or more tangible media includes one or both of processor instructions on a computer-readable storage media and special purpose hardware, such as ASIC 920.

Network link 978 typically provides information communication using transmission media through one or more networks to other devices that use or process the information. For example, network link 978 may provide a connection through local network 980 to a host computer 982 or to equipment 984 operated by an Internet Service Provider (ISP). ISP equipment 984 in turn provides data communication services through the public, world-wide packet-switching communication network of networks now commonly referred to as the Internet 990.

A computer called a server host 992 connected to the Internet hosts a process that provides a service in response to information received over the Internet. For example, server host 992 hosts a process that provides information representing video data for presentation at display 914. It is contemplated that the components of system 900 can be deployed in various configurations within other computer systems, e.g., host 982 and server 992.

At least some embodiments of the invention are related to the use of computer system 900 for implementing some or all of the techniques described herein. According to one embodiment of the invention, those techniques are performed by computer system 900 in response to processor 902 executing one or more sequences of one or more processor instructions contained in memory 904. Such instructions, also called computer instructions, software and program code, may be read into memory 904 from another computer-readable medium such as storage device 908 or network link 978. Execution of the sequences of instructions contained in memory 904 causes processor 902 to perform one or more of the method steps described herein. In alternative embodiments, hardware, such as ASIC 920, may be used in place of or in combination with software to implement the invention. Thus, embodiments of the invention are not limited to any specific combination of hardware and software, unless otherwise explicitly stated herein.

The signals transmitted over network link 978 and other networks through communications interface 970, carry information to and from computer system 900. Computer system 900 can send and receive information, including program code, through the networks 980, 990 among others, through network link 978 and communications interface 970. In an example using the Internet 990, a server host 992 transmits program code for a particular application, requested by a message sent from computer 900, through Internet 990, ISP equipment 984, local network 980 and communications interface 970. The received code may be executed by processor 902 as it is received, or may be stored in memory 904 or in storage device 908 or any other non-volatile storage for later execution, or both. In this manner, computer system 900 may obtain application program code in the form of signals on a carrier wave.

Various forms of computer readable media may be involved in carrying one or more sequence of instructions or data or both to processor 902 for execution. For example, instructions and data may initially be carried on a magnetic disk of a remote computer such as host 982. The remote computer loads the instructions and data into its dynamic memory and sends the instructions and data over a telephone line using a modem. A modem local to the computer system 900 receives the instructions and data on a telephone line and uses an infra-red transmitter to convert the instructions and data to a signal on an infra-red carrier wave serving as the network link 978. An infrared detector serving as communications interface 970 receives the instructions and data carried in the infrared signal and places information representing the instructions and data onto bus 910. Bus 910 carries the information to memory 904 from which processor 902 retrieves and executes the instructions using some of the data sent with the instructions. The instructions and data received in memory 904 may optionally be stored on storage device 908, either before or after execution by the processor 902.

Figure 10:
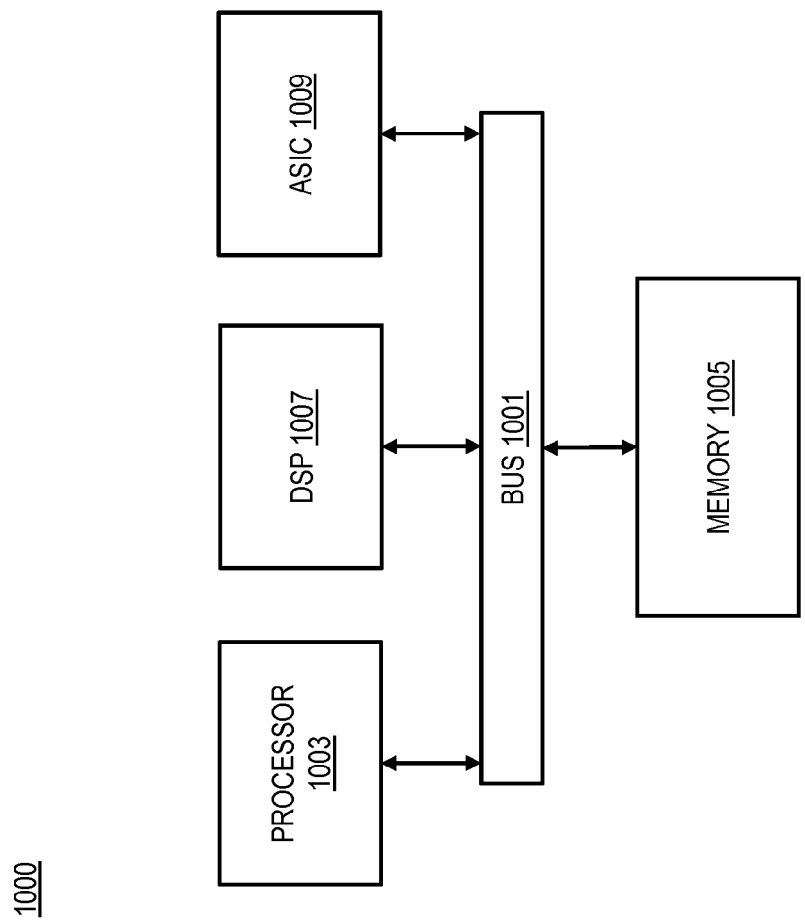
FIG. 10 is a diagram of a chip set that can be used to implement an embodiment of the invention.

FIG. 10 illustrates a chip set or chip 1000 upon which an embodiment of the invention may be implemented. Chip set 1000 is programmed to provide adaptive display and filtering of sensors and sensor data as described herein and includes, for instance, the processor and memory components described with respect to FIG. 9 incorporated in one or more physical packages (e.g., chips). By way of example, a physical package includes an arrangement of one or more materials, components, and/or wires on a structural assembly (e.g., a baseboard) to provide one or more characteristics such as physical strength, conservation of size, and/or limitation of electrical interaction. It is contemplated that in certain embodiments the chip set 1000 can be implemented in a single chip. It is further contemplated that in certain embodiments the chip set or chip 1000 can be implemented as a single "system on a chip." It is further contemplated that in certain embodiments a separate ASIC would not be used, for example, and that all relevant functions as disclosed herein would be performed by a processor or processors. Chip set or chip 1000, or a portion thereof, constitutes a means for performing one or more steps of providing user interface navigation information associated with the availability of functions. Chip set or chip 1000, or a portion thereof, constitutes a means for performing one or more steps of providing adaptive display and filtering of sensors and sensor data.

In one embodiment, the chip set or chip 1000 includes a communication mechanism such as a bus 1001 for passing information among the components of the chip set 1000. A processor 1003 has connectivity to the bus 1001 to execute instructions and process information stored in, for example, a memory 1005. The processor 1003 may include one or more processing cores with each core configured to perform independently. A multi-core processor enables multiprocessing within a single physical package. Examples of a multi-core processor include two, four, eight, or greater numbers of processing cores. Alternatively or in addition, the processor 1003 may include one or more microprocessors configured in tandem via the bus 1001 to enable independent execution of instructions, pipelining, and multithreading. The processor 1003 may also be accompanied with one or more specialized components to perform certain processing functions and tasks such as one or more digital signal processors (DSP) 1007, or one or more application-specific integrated circuits (ASIC) 1009. A DSP 1007 typically is configured to process real-world signals (e.g., sound) in real time independently of the processor 1003. Similarly, an ASIC 1009 can be configured to performed specialized functions not easily performed by a more general purpose processor. Other specialized components to aid in performing the inventive functions described herein may include one or more field programmable gate arrays (FPGA) (not shown), one or more controllers (not shown), or one or more other special-purpose computer chips.

In one embodiment, the chip set or chip 1000 includes merely one or more processors and some software and/or firmware supporting and/or relating to and/or for the one or more processors.

The processor 1003 and accompanying components have connectivity to the memory 1005 via the bus 1001. The memory 1005 includes both dynamic memory (e.g., RAM, magnetic disk, writable optical disk, etc.) and static memory (e.g., ROM, CD-ROM, etc.) for storing executable instructions that when executed perform the inventive steps described herein to provide adaptive display and filtering of sensors and sensor data. The memory 1005 also stores the data associated with or generated by the execution of the inventive steps.

Figure 11:
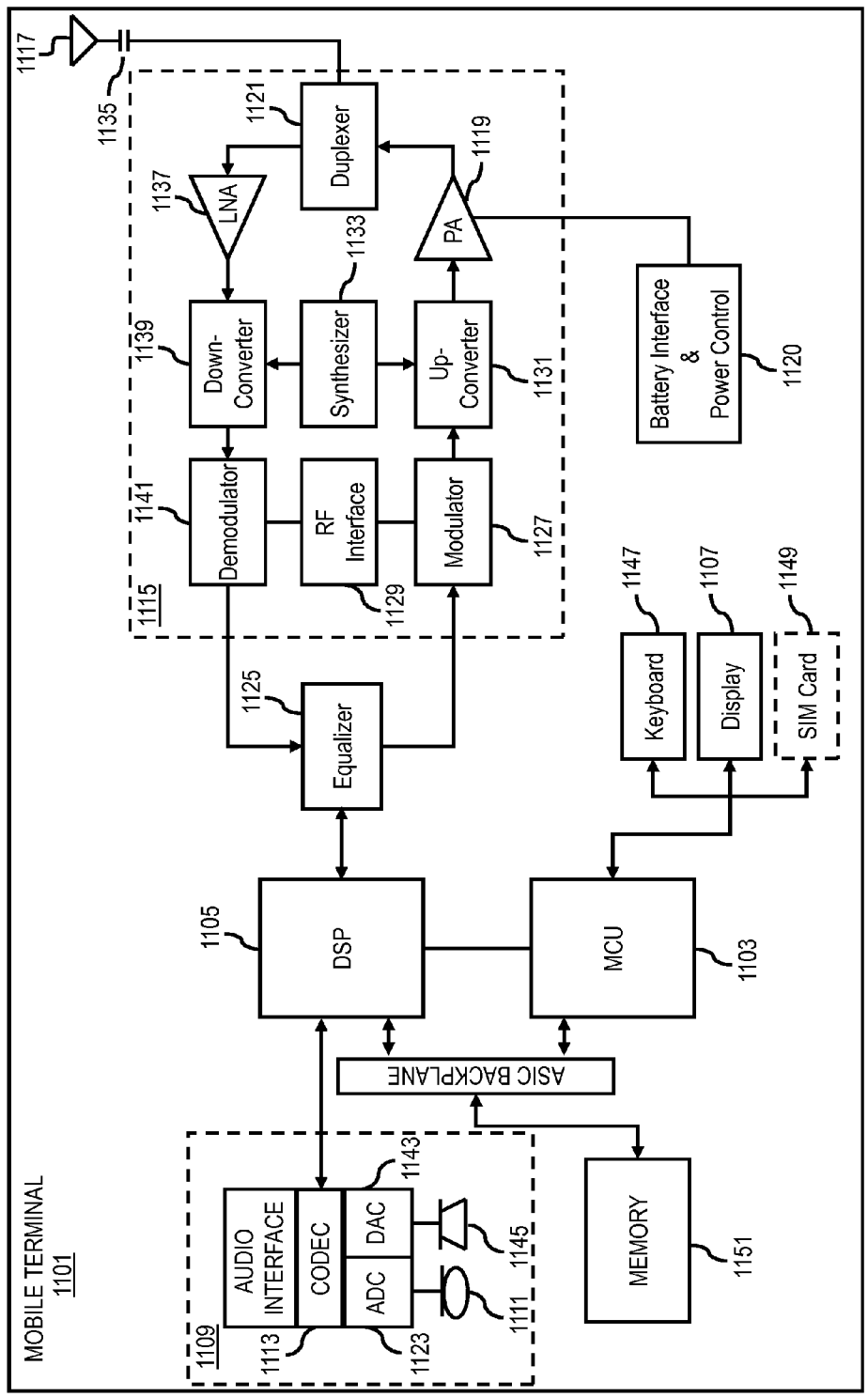
FIG. 11 is a diagram of a mobile terminal (e.g., handset) that can be used to implement an embodiment of the invention.

FIG. 11 is a diagram of exemplary components of a mobile terminal (e.g., handset) for communications, which is capable of operating in the system of FIG. 1, according to one embodiment. In some embodiments, mobile terminal 1101, or a portion thereof, constitutes a means for performing one or more steps of providing adaptive display and filtering of sensors and sensor data. Generally, a radio receiver is often defined in terms of front-end and back-end characteristics. The front-end of the receiver encompasses all of the Radio Frequency (RF) circuitry whereas the back-end encompasses all of the base-band processing circuitry. As used in this application, the term "circuitry" refers to both: (1) hardware-only implementations (such as implementations in only analog and/or digital circuitry), and (2) to combinations of circuitry and software (and/or firmware) (such as, if applicable to the particular context, to a combination of processor(s), including digital signal processor(s), software, and memory (ies) that work together to cause an apparatus, such as a mobile phone or server, to perform various functions). This definition of "circuitry" applies to all uses of this term in this application, including in any claims. As a further example, as used in this application and if applicable to the particular context, the term "circuitry" would also cover an implementation of merely a processor (or multiple processors) and its (or their) accompanying software/or firmware. The term "circuitry" would also cover if applicable to the particular context, for example, a baseband integrated circuit or applications processor integrated circuit in a mobile phone or a similar integrated circuit in a cellular network device or other network devices.

Pertinent internal components of the telephone include a Main Control Unit (MCU) 1103, a Digital Signal Processor (DSP) 1105, and a receiver/transmitter unit including a microphone gain control unit and a speaker gain control unit. A main display unit 1107 provides a display to the user in support of various applications and mobile terminal functions that perform or support the steps of providing adaptive display and filtering of sensors and sensor data. The display 1107 includes display circuitry configured to display at least a portion of a user interface of the mobile terminal (e.g., mobile telephone). Additionally, the display 1107 and display circuitry are configured to facilitate user control of at least some functions of the mobile terminal. An audio function circuitry 1109 includes a microphone 1111 and microphone amplifier that amplifies the speech signal output from the microphone 1111. The amplified speech signal output from the microphone 1111 is fed to a coder/decoder (CODEC) 1113.

A radio section 1115 amplifies power and converts frequency in order to communicate with a base station, which is included in a mobile communication system, via antenna 1117. The power amplifier (PA) 1119 and the transmitter/modulation circuitry are operationally responsive to the MCU 1103, with an output from the PA 1119 coupled to the duplexer 1121 or circulator or antenna switch, as known in the art. The PA 1119 also couples to a battery interface and power control unit 1120.

In use, a user of mobile terminal 1101 speaks into the microphone 1111 and his or her voice along with any detected background noise is converted into an analog voltage. The analog voltage is then converted into a digital signal through the Analog to Digital Converter (ADC) 1123. The control unit 1103 routes the digital signal into the DSP 1105 for processing therein, such as speech encoding, channel encoding, encrypting, and interleaving. In one embodiment, the processed voice signals are encoded, by units not separately shown, using a cellular transmission protocol such as enhanced data rates for global evolution (EDGE), general packet radio service (GPRS), global system for mobile communications (GSM), Internet protocol multimedia subsystem (IMS), universal mobile telecommunications system (UMTS), etc., as well as any other suitable wireless medium, e.g., microwave access (WiMAX), Long Term Evolution (LTE) networks, code division multiple access (CDMA), wideband code division multiple access (WCDMA), wireless fidelity (WI-FI), satellite, and the like, or any combination thereof.

The encoded signals are then routed to an equalizer 1125 for compensation of any frequency-dependent impairments that occur during transmission though the air such as phase and amplitude distortion. After equalizing the bit stream, the modulator 1127 combines the signal with a RF signal generated in the RF interface 1129. The modulator 1127 generates a sine wave by way of frequency or phase modulation. In order to prepare the signal for transmission, an up-converter 1131 combines the sine wave output from the modulator 1127 with another sine wave generated by a synthesizer 1133 to achieve the desired frequency of transmission. The signal is then sent through a PA 1119 to increase the signal to an appropriate power level. In practical systems, the PA 1119 acts as a variable gain amplifier whose gain is controlled by the DSP 1105 from information received from a network base station. The signal is then filtered within the duplexer 1121 and optionally sent to an antenna coupler 1135 to match impedances to provide maximum power transfer. Finally, the signal is transmitted via antenna 1117 to a local base station. An automatic gain control (AGC) can be supplied to control the gain of the final stages of the receiver. The signals may be forwarded from there to a remote telephone which may be another cellular telephone, any other mobile phone or a landline connected to a Public Switched Telephone Network (PSTN), or other telephony networks.

Voice signals transmitted to the mobile terminal 1101 are received via antenna 1117 and immediately amplified by a low noise amplifier (LNA) 1137. A down-converter 1139 lowers the carrier frequency while the demodulator 1141 strips away the RF leaving only a digital bit stream. The signal then goes through the equalizer 1125 and is processed by the DSP 1105. A Digital to Analog Converter (DAC) 1143 converts the signal and the resulting output is transmitted to the user through the speaker 1145, all under control of a Main Control Unit (MCU) 1103 which can be implemented as a Central Processing Unit (CPU) (not shown).

The MCU 1103 receives various signals including input signals from the keyboard 1147. The keyboard 1147 and/or the MCU 1103 in combination with other user input components (e.g., the microphone 1111) comprise a user interface circuitry for managing user input. The MCU 1103 runs a user interface software to facilitate user control of at least some functions of the mobile terminal 1101 to provide adaptive display and filtering of sensors and sensor data. The MCU 1103 also delivers a display command and a switch command to the display 1107 and to the speech output switching controller, respectively. Further, the MCU 1103 exchanges information with the DSP 1105 and can access an optionally incorporated SIM card 1149 and a memory 1151. In addition, the MCU 1103 executes various control functions required of the terminal. The DSP 1105 may, depending upon the implementation, perform any of a variety of conventional digital processing functions on the voice signals. Additionally, DSP 1105 determines the background noise level of the local environment from the signals detected by microphone 1111 and sets the gain of microphone 1111 to a level selected to compensate for the natural tendency of the user of the mobile terminal 1101.

The CODEC 1113 includes the ADC 1123 and DAC 1143. The memory 1151 stores various data including call incoming tone data and is capable of storing other data including music data received via, e.g., the global Internet. The software module could reside in RAM memory, flash memory, registers, or any other form of writable storage medium known in the art. The memory device 1151 may be, but not limited to, a single memory, CD, DVD, ROM, RAM, EEPROM, optical storage, magnetic disk storage, flash memory storage, or any other non-volatile storage medium capable of storing digital data.

An optionally incorporated SIM card 1149 carries, for instance, important information, such as the cellular phone number, the carrier supplying service, subscription details, and security information. The SIM card 1149 serves primarily to identify the mobile terminal 1101 on a radio network. The card 1149 also contains a memory for storing a personal telephone number registry, text messages, and user specific mobile terminal settings.

While the invention has been described in connection with a number of embodiments and implementations, the invention is not so limited but covers various obvious modifications and equivalent arrangements, which fall within the purview of the appended claims. Although features of the invention are expressed in certain combinations among the claims, it is contemplated that these features can be arranged in any combination and order.

What is claimed is:

1. A method comprising facilitating a processing of and/or processing (1) data and/or (2) information and/or (3) at least one signal, the (1) data and/or (2) information and/or (3) at least one signal based, at least in part, on the following:
   one or more signals associated with one or more sensors, the one or more sensors associated with determining at least one operational state of one or more other sensors;
   a processing of the one or more signals for comparison against one or more predetermined signals; and
   one or more parameters for one or more filters based, at least in part, on the comparison,
   wherein the one or more filters operate, at least in part, on the one or more sensors, one or more other signals determined from the one or more other sensors, or a combination thereof,
   transmitting, via a transceiver, the one or more signals.

2. A method of claim 1, wherein the (1) data and/or (2) information and/or (3) at least one signal are further based, at least in part, on the following:
   a processing of the one or more predetermined signals to determine the one or more parameters; and
   an association of the one or more parameters to the one or more predetermined signals.

3. A method of claim 1, wherein the (1) data and/or (2) information and/or (3) at least one signal are further based, at least in part, on the following:
   a processing of the one or more predetermined signals to generate one or more models,
   wherein the comparison of the one or more signals against the one or more predetermined signals is based, at least in part, on the one or more models.

4. A method of claim 1, wherein the one or more signals, the one or more predetermined signals, the one or more other signals, or a combination include, at least in part, (a) one or more movement signals; (b) one or more physiological signals; (c) one or more models of the one or more movement signals, the one or more physiological signals, or a combination thereof; or (d) a combination thereof.

5. A method of claim 1, wherein the one or more filters include, at least in part, one or more adaptive filters, and wherein the one or more parameters include, at least in part, initiation data, one or more coefficients determined from the initiation data, or a combination thereof.

6. A method of claim 1, wherein the (1) data and/or (2) information and/or (3) at least one signal are further based, at least in part, on the following:
   a processing of the one or more signals, the one or more predetermined signals, or a combination thereof into one or more classes,
   wherein the comparison is based, at least in part, on the one or more classes.

7. A method of claim 2, wherein the one or more filters are associated with at least one of the one or more classes.

8. A method of claim 1, wherein the (1) data and/or (2) information and/or (3) at least one signal are further based, at least in part, on the following:
   at least one determination of a beginning of a sampling period for the one or more other sensors; and
   an initiation of the determining of the one or more signals, the processing of the one or more signals, the determination of the one or more parameters, or a combination thereof based, at least in part, on the determining of the beginning of the sampling period.

9. A method of claim 8, wherein the (1) data and/or (2) information and/or (3) at least one signal are further based, at least in part, on the following:
   a processing of the one or more signals to determine one or more movement states for the sampling period; and
   at least one determination of the one or more parameters based, at least in part, on the one or more movement states.

10. A method of claim 9, wherein the (1) data and/or (2) information and/or (3) at least one signal are further based, at least in part, on the following:
    a monitoring of the one or more signals periodically, continuously, according to a schedule, on demand, or a combination thereof; and
    one or more updates to the one or more movement states based, at least in part, on the monitoring.

11. A method of claim 1, wherein the (1) data and/or (2) information and/or (3) at least one signal are further based, at least in part, on the following:
    a processing of the one more signals for determining one or more user interface states for presenting one or more sensor data at a device, at the one or more sensors, or a combination thereof.

12. A method of claim 11, wherein the (1) data and/or (2) information and/or (3) at least one signal are further based, at least in part, on the following:
    at least one determination of the one or more user interface states based, at least in part, on one or more prior user interface states, one or more user preferences, one or more configurations of one or more devices, or a combination thereof.

13. A method of claim 11, wherein the (1) data and/or (2) information and/or (3) at least one signal are further based, at least in part, on the following:
    at least one determination of the one or user interface states based, at least in part, on one or more status information items associated with the one or more devices, one or more user interactions, or a combination thereof.

14. An apparatus comprising:
    at least one processor;
    at least one memory including computer program code, and
    a transceiver configured to transmit the one or more signals,
    the at least one memory and the computer program code configured to, with the at least one processor, cause the apparatus to perform at least the following,
    determine one or more signals associated with one or more sensors, the one or more sensors associated with determining at least one operational state of one or more other sensors;
    process and/or facilitate a processing of the one or more signals for comparison against one or more predetermined signals; and
    determine one or more parameters for one or more filters based, at least in part, on the comparison,
    wherein the one or more filters operate, at least in part, on the one or more sensors, one or more other signals determined from the one or more other sensors, or a combination thereof.

15. An apparatus of claim 14, wherein the apparatus is further caused to:
    process and/or facilitate a processing of the one or more predetermined signals to determine the one or more parameters; and
    cause, at least in part, an association of the one or more parameters to the one or more predetermined signals.

16. An apparatus of claim 14, wherein the apparatus is further caused to:
    process and/or facilitate a processing of the one or more predetermined signals to generate one or more models,
    wherein the comparison of the one or more signals against the one or more predetermined signals is based, at least in part, on the one or more models.

17. An apparatus of claim 14, wherein the one or more signals, the one or more predetermined signals, the one or more other signals, or a combination include, at least in part, (a) one or more movement signals; (b) one or more physiological signals; (c) one or more models of the one or more movement signals, the one or more physiological signals, or a combination thereof; or (d) a combination thereof.

18. An apparatus of claim 14, wherein the one or more filters include, at least in part, one or more adaptive filters, and wherein the one or more parameters include, at least in part, initiation data, one or more coefficients determined from the initiation data, or a combination thereof.

19. An apparatus of claim 14, wherein the apparatus is further caused to:
process and/or facilitate a processing of the one or more signals, the one or more predetermined signals, or a combination thereof into one or more classes, wherein the comparison is based, at least in part, on the one or more classes.

20. An apparatus of claim 19, wherein the one or more filters are associated with at least one of the one or more classes.

21. An apparatus of claim 14, wherein the apparatus is further caused to:
determine a beginning of a sampling period for the one or more other sensors; and
cause, at least in part, an initiation of the determining of the one or more signals, the processing of the one or more signals, the determination of the one or more parameters, or a combination thereof based, at least in part, on the determining of the beginning of the sampling period.

22. An apparatus of claim 21, wherein the apparatus is further caused to:
process and/or facilitate a processing of the one or more signals to determine one or more movement states for the sampling period; and
determine the one or more parameters based, at least in part, on the one or more movement states.

23. An apparatus of claim 22, wherein the apparatus is further caused to:
cause, at least in part, a monitoring of the one or more signals periodically, continuously, according to a schedule, on demand, or a combination thereof; and
determine one or more updates to the one or more movement states based, at least in part, on the monitoring.

24. An apparatus of claim 14, wherein the apparatus is further caused to:
process and/or facilitate a processing of the one more signals for determining one or more user interface states for presenting one or more sensor data at a device, at the one or more sensors, or a combination thereof.

25. An apparatus of claim 24, wherein the apparatus is further caused to:
determine the one or more user interface states based, at least in part, on one or more prior user interface states, one or more user preferences, one or more configurations of one or more devices, or a combination thereof.

26. An apparatus of claim 24, wherein the apparatus is further caused to:
determine the one or user interface states based, at least in part, on one or more status information items associated with the one or more devices, one or more user interactions, or a combination thereof.

* * * * *